US012601065B2

(12) United States Patent
Vignolo et al.

(10) Patent No.: US 12,601,065 B2
(45) Date of Patent: Apr. 14, 2026

(54) CLEANING PLANT FOR METAL PRODUCTS

(71) Applicant: Danieli & C. Officine Meccaniche S.p.A., Buttrio (IT)

(72) Inventors: Luciano Vignolo, Udine (IT);
Alessandra Primavera, Faedis (IT);
Emanuele Trucillo, Udine (IT)

(73) Assignee: DANIELI & C. OFFICINE MECCANICHE S.P.A., Buttrio (IT)

( * ) Notice: Subject to any disclaimer, the term of this patent is extended or adjusted under 35 U.S.C. 154(b) by 101 days.

(21) Appl. No.: 18/554,143

(22) PCT Filed: Apr. 7, 2022

(86) PCT No.: PCT/IB2022/053283
§ 371 (c)(1),
(2) Date: Oct. 5, 2023

(87) PCT Pub. No.: WO2022/215035
PCT Pub. Date: Oct. 13, 2022

(65) Prior Publication Data
US 2024/0376609 A1      Nov. 14, 2024

(30) Foreign Application Priority Data

Apr. 7, 2021      (IT) ........................ 102021000008597

(51) Int. Cl.
C23G 3/02        (2006.01)
G01B 11/06      (2006.01)
(Continued)

(52) U.S. Cl.
CPC ............. C23G 3/025 (2013.01); C23G 3/021 (2013.01); G01B 11/0616 (2013.01); G01N 25/18 (2013.01); G01N 33/0027 (2013.01)

(58) Field of Classification Search
None
See application file for complete search history.

(56) References Cited

U.S. PATENT DOCUMENTS

2008/0066863 A1*    3/2008    Kiyose .............. H01L 21/67086
156/345.15

FOREIGN PATENT DOCUMENTS

BE        1015893 A3 *  11/2005    ............. C23G 3/024
EP        3631049 A1      4/2020
(Continued)

OTHER PUBLICATIONS

English Machine Translation of BE1015893A3.*
(Continued)

*Primary Examiner* — Kaj K Olsen
*Assistant Examiner* — Pradhuman Parihar
(74) *Attorney, Agent, or Firm* — Stetina Garred Brucker & Newboles

(57)        ABSTRACT

A cleaning plant for hot-rolled metal strips provided with a surface oxide layer, the plant comprising unwinding means for unwinding at least one coil of rolled strip and pickling means for pickling said rolled strip; wherein there are provided measuring means for measuring the thickness of the surface oxide layer, arranged between said unwinding means and said pickling means; and wherein gaseous hydrogen detection means are provided to detect the presence of gaseous hydrogen in fumes produced by said pickling means. A corresponding cleaning method is also claimed.

17 Claims, 3 Drawing Sheets

(51) Int. Cl.
    *G01N 25/18*       (2006.01)
    *G01N 33/00*       (2006.01)

(56)             References Cited

FOREIGN PATENT DOCUMENTS

| | | | |
|---|---|---|---|
| EP | 3631049 B1 * | 10/2021 | ............. B21B 45/06 |
| WO | WO0161073 | 2/2001 | |

OTHER PUBLICATIONS

Patent Cooperation Treaty, International Search Report and Written Opinion for International Application No. PCT/IB2022/053283, Jul. 11, 2022, 15 pages.
Chinese Office Action for Application No. 202280038274.2; mailed Jul. 25, 2025.

\* cited by examiner

CLEANING PLANT FOR METAL PRODUCTS

CROSS-REFERENCE TO RELATED APPLICATIONS

This application claims priority to PCT International Application No. PCT/IB2022/053283 filed on Apr. 7, 2022, which applications claims priority to Italian Patent Application No. 102021000008597 filed on Apr. 7, 2021, the entire disclosures of which are expressly incorporated herein by reference.

STATEMENT RE: FEDERALLY SPONSORED RESEARCH/DEVELOPMENT

Not Applicable

BACKGROUND

Field of the Invention

The present invention relates to a cleaning plant for oxidized metal products, in particular hot-rolled strips, and a cleaning method thereof.

Background Art

Conventional strip cleaning lines aim to remove the surface oxide layer which is created on hot-rolled metal products. Indeed, during the hot-rolling process, the slabs, either shaped by the continuous casting machine or introduced into the line from an external station by means of a reheating furnace in that known as hot charging, are rolled and reduced in thickness to define a first strip of a thickness generally comprised between 0.8 and 12 mm.

Since hot rolling is carried out at high temperatures, and after rolling the strip is wound at a temperature comprised between 200° C. and 750° C. as a function of the chemical composition and the use of the final product, several stretches of the surface of the metal product are exposed to oxidizing agents, such as air and water. Indeed, it is not possible to treat the metal strip in an inert atmosphere and this causes the oxidation of the surface layers of the product which, in addition to determining a finished material weight loss, is also a problem to be solved in a subsequent finishing process because the oxide formed can damage the surface quality of the product during cold rolling and/or during painting. This oxide layer generally consists of ferrous oxide in the part closest to the metal, i.e., in the innermost part, and of magnetite and hematite outwards.

Furthermore, the finishing process is generally not performed immediately downstream of the hot-rolling process. The hot-rolled strip is usually wound into coils of the desired weight or diameter (dependent on the strip thickness exiting from the rolling line) and allowed to cool to ambient temperature in warehouses arranged near the hot-rolling line. This can therefore cause further oxidation of the strip surfaces.

Sometimes, the hot rolling and pickling take place in different sites, so the strip coils can be transported in conditions which are very aggressive from the point of view of the corrosive attack, e.g., in the presence of salty air if transported by ship.

However, if this layer of oxides, generally known as scale or flake, were to remain intact and adhere firmly to the metal strip, it would perform a protective action of the latter. However, due both to the action of the atmospheric agents during transport and storage, and to the inevitable breakage of the scale itself, it is difficult to keep the oxide layer intact.

Furthermore, moisture penetrates the cracks and reacts with the ferrous oxide layer closest to the metal surface, e.g., steel, forming ferrous and ferric hydroxides which, due to the increase in volume, cause further detachment of the oxide layer, thus allowing the attack on another part of the metal.

The hot-rolled strip must be finalized in the finishing line at a later stage, according to the production requirements.

Said strip can remain in a warehouse even for several days before being finalized, so it has had plenty of time to cool down and reach ambient temperature, determining the production of oxide layers which can reach 5-20 µm per side of the strip, for example. The thickness of the oxide is directly proportional to the nominal thickness of the strip, but also to the temperature of the strip during its winding.

It is therefore necessary to clean the oxide coating from the material before carrying out the cold-rolling treatments of the product and the subsequent coating (e.g., galvanizing or tin-plating, painting, etc.). This is especially important because this oxide layer, or scale, can damage the surface quality of the finished product and make rolling difficult.

In the current art, the strip is cleaned by means of special layouts of the descaling and pickling line, which usually precede the cold rolling. Normally, there is provided an unwinding line for the previously hot-rolled strip, followed by a device to break the scale so that it can be more easily removed by means of subsequent treatments. The scale is cleaned from the product through consecutive steps, which include the introduction of the product in tanks of acid (chemical pickling). The product can then be brushed and rinsed.

The current economic situation and environmental needs are increasingly driving manufacturers to apply methods or technologies adapted to optimize the process controls while minimizing energy consumption, product consumption, such as pickling acids, and processing waste intended as material yield and material quality yield.

However, it is currently not possible to precisely identify a priori the optimal process parameters to remove the exact amount of oxide with the minimum amount of acid.

Disadvantageously, it is instead very likely that more acid than necessary will be used, even removing a part of the "good" product, i.e., a part of the base metal of the strip, to be sure of a successful cleaning, but at the cost of production efficiency. Indeed, pickling process operators often prefer the production of slightly over-pickled strips to avoid quality rejection if residues of under-pickled oxide not removed by the previous chemical attack are still present at the pickling means outlet.

An over-pickled strip has the following disadvantages inter alia:

a reduced production capacity of the plant;

a greater drop in yield by the effect of the chemical attack;

a different surface quality (roughness) of one same strip, which can negatively influence the subsequent rolling and coating processes of the strip;

the increased use of consumables.

On the contrary, in the case of an under-pickled strip, it is possible that the acid used or the permanence time in the treatment tanks has not been sufficient. Therefore, the strip is not optimally cleaned and must be discarded/declassified or reprocessed.

Furthermore, the evolution of steel grades required to meet ever-increasing performance requirements, such as an increase in elastic and tensile strength and percentage of elongation at break, have complicated the chemical treatments to be performed on these categories of steel.

For example, the gradual but strong drive to shift from hydrocarbon-based energy mobility to electric mobility is increasing the production of non-grain oriented sheets, which are characterized by the high presence of silicon in the alloy, and, disadvantageously, silicon oxides are particularly difficult to remove in pickling tanks.

This greatly influences the chemical pickling process, which in the future will have to be flexible and allow a quick change of the reaction kinetics for the various and different products to be treated.

The need to provide an innovative cleaning plant for metal strips capable of overcoming the aforesaid drawbacks is thus felt.

SUMMARY OF THE INVENTION

It is an object of the present invention to provide a cleaning plant for metal strips which allows detecting a plurality of data useful to operators to optimally adjust, preferably automatically, the operating parameters of chemical pickling, making the latter highly precise, cost-effective, and ecologically sustainable.

It is a further object of the invention to provide a plant for detecting and processing said plurality of data in real-time to automatically and instantaneously adjust the operating parameters of pickling, thus achieving an accurate control of the chemical pickling process and, thus, further improving the pickling conditions as compared to the solutions of the prior art.

The automatic adjustment of the pickling parameters is achieved, for example, by means of software for simulating the oxide layer along the strip and controlling the pickling kinetics.

The solution of the invention is highly flexible and allows the quick variation of the reaction kinetics even with different products to be processed.

The present invention thus achieves at least one of the objects discussed above by a cleaning plant for cleaning rolled metal strips provided with an oxide surface layer, said plant, according to claim 1, comprising unwinding means for unwinding at least one coil of rolled strip;

chemical pickling means for pickling said rolled strip;

measuring means for measuring the thickness of the surface oxide layer, arranged between said unwinding means and said chemical pickling means;

wherein said measuring means comprise at least one laser source cooperating with an optical fiber spectrometer, defining a LIBS (Laser-Induced Breakdown Spectroscopy) system adapted to analyze the oxide composition in addition to thickness;

wherein gaseous hydrogen detection means are provided to detect the presence of gaseous hydrogen in fumes produced by said chemical pickling means;

and wherein a processing unit is provided, adapted to process data at least from said measuring means and said gaseous hydrogen detection means, and adapted to adjust operating parameters of said chemical pickling means, defining the optimal conditions of the pickling process.

A further aspect of the invention relates to a method of cleaning metal strips to be performed by the aforesaid plant which, according to claim 14, comprises the following steps:

a) unwinding at least one coil of rolled strip by means of the unwinding means;

b) measuring the thickness of the surface oxide layer of the rolled strip by means of the measuring means;

c) pickling said rolled strip by means of the chemical pickling means;

where, in step b), the measurement of the thickness of the oxide surface layer is carried out, together with an analysis of the oxide composition, by at least one laser source associated with an optical fiber spectrometer, defining a LIBS (Laser-Induced Breakdown Spectroscopy) system; wherein said optical fiber spectrometer measures the presence of oxygen while the laser of said laser source penetrates the oxide surface layer placed on the strip until the non-oxidized base material is reached, and the thickness of the oxide surface layer is equal to the depth excavated in said oxide layer, by means of the laser source, when said spectrometer detects the absence of oxygen;

wherein, in step c), there is provided the detection of gaseous hydrogen in the fumes produced by said chemical pickling means by means of the gaseous hydrogen detection means;

and wherein there are provided the processing of data from both said measuring means and said gaseous hydrogen detection means and, accordingly, the adjustment of the operating parameters of said chemical pickling means, by means of the processing unit.

Advantageously, the plant and method of the invention allow:

maximizing the production capacity of chemical pickling means;

improving material yield by minimizing the acid attack on the oxide-free surface of the strip;

improving product quality by eliminating over- or under-pickled stretches of strip;

optimizing energy and acid consumption.

The knowledge, by measurement, of the oxide layer thickness and the $O_2$/Fe ratio, and the detection of gaseous hydrogen in the fumes emitted from the acid pickling tanks allow greater flexibility and optimal estimation of the pickling parameter adjustment. The optimization of the process control, determined by the combined processing of the data detected by means of at least one LIBS system and the gaseous hydrogen detection means in the fumes, advantageously allows minimizing, at the same time, energy consumption, product consumption, such as pickling acid, and processing waste intended as material yield and material quality yield.

The oxide layer thickness is measured by a technology known as LIBS (Laser-Induced Breakdown Spectroscopy) which uses a pulsed laser to achieve the removal and vaporization of the oxide layer. The oxide phase change from the solid to the gaseous state generates a plasma state and, through the reading of the radiation emitted by the de-excitation of the excited species by means of a spectrometer, allow identifying the various elements present in the oxidized layer. It is confirmed that the base material has been reached when the spectrum of the oxidized layer has no more oxygen, and the thickness of the oxidized layer can be defined knowing the number of pulses emitted by the laser up to that moment.

The knowledge of the chemical reactions occurring in pickling tanks, in which for example hydrochloric acid (used in particular for pickling low/medium carbon steel strip) is mainly used, has provided interesting indications for evaluating the chemical attack combinations of the unoxidized base material. The reactions which occur are as follows:

$$FeO+2HCl \rightarrow FeCl_2+H_2O \qquad \qquad 1)$$

$$Fc_2O_3+6HCl \rightarrow 2FeCl_3+3H_2O \qquad \qquad 2)$$

$$Fc_3O_4+8HCl \rightarrow FeCl_2+2FeCl_3+4H_2O \qquad \qquad 3)$$

$$Fe+2HCl \rightarrow FeCl_2+H_2(gas) \qquad \qquad 4)$$

Reactions 1) to 3) represent the effect of the presence of the various types of oxide in the reaction, while reaction 4) shows that when an acid reacts with iron, without the presence of oxide, the result of the reaction comprises the development of hydrogen in gaseous form. From this observation, it was decided to measure the amount of hydrogen present in the fumes, in order to use this value as a parameter for evaluating the extent of the pickling process and advantageously in combination with the data on the oxide layer detected by means of the LIBS system.

In a first variant of the invention, there is provided the detection of any residual oxides on the strip by means of first optical detection means arranged at the inlet of the last chemical pickling tank. This allows the operating parameters of pickling of the last pickling tank to be changed, further minimizing the quality waste. Indeed, the presence of oxide residues clearly visible on the surface of the strip allows evaluating the level of under-pickling and intervening promptly, by virtue of the aforesaid software for optimizing the pickling conditions, on the pickling parameters of the last pickling tank, such as the travel speed, and thus the strip feeding speed, and/or the turbulence level of the acid solution present in the last tank.

In a second variant of the invention, there is provided the detection, by means of second optical detection means arranged downstream of the pickling means, of properties of the strip surface, such as surface roughness and/or reflectivity and/or gray level and/or emissivity. These properties are an indicator of the level of over-pickling of the material. Indeed, the acid attack on an oxide-free surface changes its roughness but also its crystalline texture by the effect of the different attack on the edge of the crystalline grains. This feedback allows, by means of the pickling optimization software, the operating parameters of pickling to be modified upstream of the pickling line, further minimizing quality waste.

In a third variant of the invention, there is provided the detection of any residual oxides on the strip by means of third optical detection means arranged downstream of the pickling means. This feedback also allows, by means of the pickling optimization software, the operating parameters of pickling to be modified upstream of the pickling line, again further minimizing quality waste.

In a fourth variant of the invention, there is provided a mass balance, using acid and iron concentration analyzers, in the spent acid solution and the regenerated acid solution, which are continuously moved from and to the pickling means, respectively, thus allowing further refinement of pickling control.

The features of some or all of the variants of the invention can be advantageously combined.

In general, in case of over-pickling, the operating parameters of pickling can be modified as follows:
  increasing the process speed if plant conditions permit (increase in production capacity);
  reducing the bath turbulence to decrease reaction kinetics (decrease in energy consumption);
  reducing the bath temperature to decrease reaction kinetics (decrease in energy consumption);

decreasing acid concentration (decrease in acid consumption).

In the case of under-pickling, instead, the operating parameters of pickling can be modified as follows:
  decreasing the process speed (decrease in production capacity);
  increasing the bath turbulence to increase reaction kinetics;
  increasing the bath temperature to increase reaction kinetics;
  increasing the acid concentration.

The dependent claims describe preferred embodiments of the invention.

BRIEF DESCRIPTION OF THE FIGURES

Further features and advantages of the invention will be more apparent in the light of the detailed description of a preferred, but not exclusive, embodiments of a cleaning plant of metal strips illustrated by the way of non-limiting example, with the help of the accompanying drawings in which.

DETAILED DESCRIPTION OF EXAMPLE EMBODIMENTS OF THE INVENTION

Figure 1:
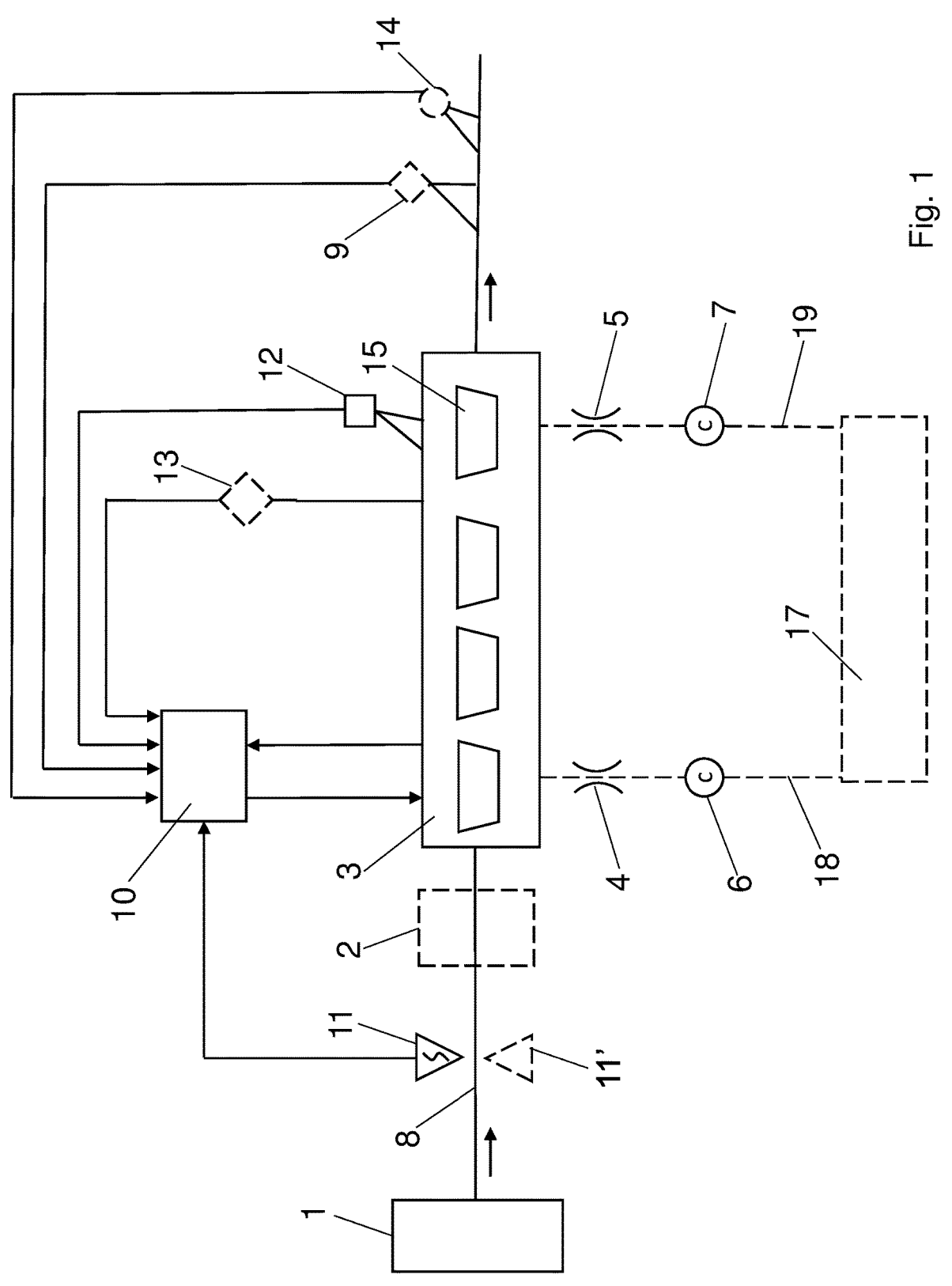
FIG. 1 shows a diagrammatic view of an embodiment of a plant according to the invention.

The figures show some examples of embodiments of a cleaning plant for oxidized metal strips. In particular, the dashed components in FIG. 1 can be optional, considered individually or together.

The plant according to the present invention, in all its embodiments, comprises in sequence:
  unwinding means 1 for unwinding at least one coil of rolled strip having an oxide surface layer;
  measuring means 11 for measuring the thickness of the oxide surface layer;
  chemical pickling means 3 for pickling the rolled strip.

In a first variant, the unwinding means 1 comprise a single rolled strip unwinding line, preferably a single unwinding reel.

In a second variant of the unwinding means 1, there is provided a double unwinding line for rolled strips followed by a cutting and welding machine to give continuity to the unwound strip to be pickled.

In particular, there can be provided at least two unwinding reels and a welding machine, preferably a laser welding machine, capable of producing joints between the strips unwound by the unwinding reels, thus defining a continuous strip, i.e., allowing a continuous supply of metal strip downstream of the unwinding means. A tensioning device can optionally be provided to adjust the strip tension.

Possible storage systems (not shown) are provided upstream and/or downstream of the chemical pickling means 3.

Preferably, between the unwinding means 1 and the pickling means 5, at least one scale breaking device 3 can be advantageously provided, said scale breaking device using, for example, mechanical systems for breaking the oxide layer, to make this latter more removable by means of subsequent chemical pickling means.

The measuring means 11 for measuring the thickness of the oxide layer comprise, in particular consist of, at least one laser source cooperating with an optical fiber spectrometer, defining a LIBS (Laser-Induced Breakdown Spectroscopy) system also adapted to analyze the oxide composition and/or the concentration of the oxide constituent elements. The term oxide composition refers to the chemical nature of the individual oxide or mixtures of oxides. The term concentration of oxide constituent elements refers to the concentration of the individual ionic species constituting the individual oxide.

Advantageously said fiber-optic spectrometer is configured to measure the presence of oxygen as the laser from the laser source penetrates the oxide layer present on the surface of the rolled strip towards the unoxidized base material.

The system uses the laser source for the point ablation of the oxide layer. The laser source provides the energy necessary to take the species, belonging to the oxide layer removed by ablation along the thickness thereof, to the plasma state. The de-excitation of the ions constituting the plasma allows, through the use of the spectrometer, both the identification of the species present and the concentration thereof. The thickness of the oxide layer is advantageously detected at the disappearance of the oxygen signal.

Therefore, the fiber optic spectrometer can measure the presence of oxygen during point ablation of the oxide layer. When the spectrometer detects after a time "t" of erosion, thus during ablation, the absence of oxygen, the measurement of the depth of the eroded layer of material at time "t" will correspond to the thickness of the oxide surface layer.

In other words, a software calculates the erosion depth which will be equal to the thickness of the oxide surface layer at the disappearance of the oxygen peak, the time "t" of erosion and the erosion speed being known.

By virtue of the spectrometric measurement, it is possible to know both the thickness of the oxide layer and the composition thereof (e.g., $O_2$/Fe ratio). By virtue of these data, it becomes possible to optimally define the operating parameters of pickling using an optimization software for optimizing the kinetics of the pickling process. An additional advantage of using LIBS technology is due to its minimal invasiveness, being a micro-destructive technology in that the only damage caused is the ablation of the material which creates a cavity with dimensions depending on the focused laser spot.

In an advantageous variant, there are provided two or more measuring means 11, 11' arranged above and below the feeding line of the rolled strip, to calculate the thickness of the oxide layer on both the upper face and the lower face of the strip and the difference between the edge and center of the strip.

In particular, there are provided at least one measuring means 11 arranged above the feeding line of the rolled strip 8 and at least one measuring means 11' arranged below the feeding line of the rolled strip 8.

When two or more measurement means 11 and two or more measurement means 11' are provided, at least four or more laser sources associated with a respective fiber optic spectrometer are provided, defining four or more LIBS systems.

The measuring means 11, and thus the LIBS system or the LIBS systems, can be arranged in a fixed or movable manner with respect to the feeding line of the rolled strip 8. The thickness of the oxide layer can be measured in several ways.

For example, it is possible to perform the measurement statically, temporarily interrupting the strip inflow to the cleaning plant (e.g., during the welding of the strips) and restarting once the data are obtained.

Alternatively, the measurement can be carried out continuously, e.g., by arranging the measuring means 11 on carriages adapted to be moved together with the metal strip.

Advantageously, in all the embodiments of the plant of the invention, gaseous hydrogen detection means 12 are provided to detect the presence of gaseous hydrogen in the fumes produced by said chemical pickling means 3.

Such gaseous hydrogen detection means 12 either comprise or consist of a detection instrument adapted to perform thermal conductivity measurements. For example, such gaseous hydrogen detection means 12 comprise one, two or more thermal conductivity detectors.

Figure 3:
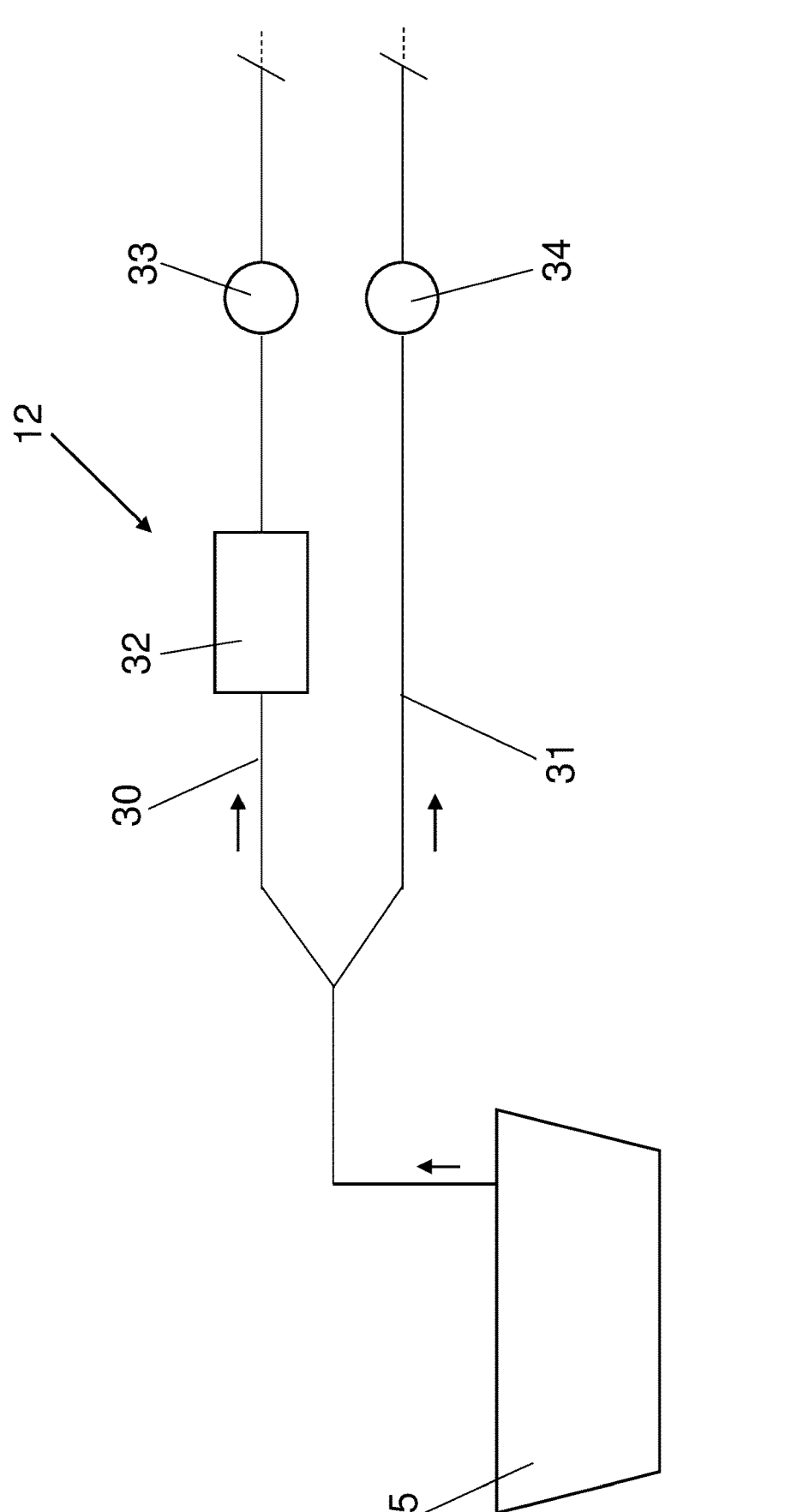
FIG. 3 shows a diagrammatic view of a part of the system of the invention.

In particular, detection instrument can be used comprising (FIG. 3):

two conduits 30, 31, into which the flow of fumes produced by a pickling tank 15 is divided and advanced;

a combustion chamber 32, such as a catalytic furnace, arranged along one of said two conduits, such as the conduit 30, for the ignition of the combustion so that the hydrogen, if any, is burned in the fume flow of the related conduit 30;

thermal conductivity detectors 33, 34 to detect a possible difference in thermal conductivity between the flows of the two conduits, downstream of the combustion chamber 32.

If a difference in thermal conductivity is detected between the flows of the two conduits, this would confirm the presence of gaseous hydrogen in the fumes, and thus an over-pickling of the strip surface.

In the combustion chamber, since the temperature of the fumes is generally below 80° C., a spark can be ignited to burn gaseous hydrogen, which is the only component reactive to the spark.

The measurement of gaseous hydrogen present in the fumes produced by chemical pickling means is thus obtained by comparison of the two thermal conductivity signals emitted by the conductivity detectors (in the sample gas and the reference gas without hydrogen) thus obtaining a high accuracy of the measurement.

Preferably, the chemical pickling means 3 comprise two or more chemical pickling tanks, containing an acid solution, arranged in sequence. The gaseous hydrogen detection means 12 can be positioned to detect the presence of gaseous hydrogen in the fumes produced by at least the last chemical pickling tank 15, preferably in the fumes produced by only the last tank 15 between said two or more chemical pickling tanks.

In a variant of the plant of the invention, there are provided first optical detection means 13, arranged at the inlet of said last chemical pickling tank 15, to detect any residual oxide on the surface of the strip. Such first detection means 13 comprise, for example, at least one system for the video analysis of the strip, which can include one or more cameras with a possible corresponding lighting system allowing, if any oxide residues are visible on the surface of the strip, to modify by virtue of the aforementioned software the operating parameters of pickling of the last pickling tank 15, further minimizing the quality reject due to underpickling in a surprisingly optimal manner. In particular, one or more cameras are provided to analyze three different areas of the strip surface, such as the operator edge, motor edge and center.

This video analysis system allows, for example, comparing the color or brightness of the strip with chromatic scales indicating different cleaning degrees of the product, previously loaded into the memory of a processing unit 10. By using digital cameras with high pixel density, for example, it is possible to define the ratio of the defective area to the pickled area for each square meter of strip, the minimum and maximum sizes of the defective areas and the position thereof on the strip (upper surface/lower surface, center/edge, head/tail or coil body, i.e., the part of the strip between head and tail).

Optionally, second optical detection means 14, arranged downstream of the chemical pickling means 3, can be provided to detect properties such as surface roughness and/or reflectivity and/or gray level and/or emissivity of at least one surface of the strip. Such second optical detection means 14 comprise, for example, an optical sensor adapted to detect any residual surface effects, signs of over pickling of the surface. This feedback also allows modifying the operating parameters of pickling upstream, thus minimizing the quality deviation.

For example, such a sensor is a pyrometer which measures the emissivity of the pickled surface, which represents the ability of a surface to absorb heat and then transmit such an energy by emitting it in the infrared range.

The action of the acid on the metal surface of the strip modifies the surface roughness and consequently also the emissivity, which becomes an index to define possible effects of under-pickling or over-pickling of the strip surface.

Third optical detection means 9, also arranged downstream of the chemical pickling means 3, can also be provided to detect any residual oxide on the strip surface. This feedback also allows modifying the operating parameters of pickling upstream, thus minimizing the quality deviation due to possible under-pickling. The third optical detection means 9 can comprise a video analysis system similar to that of the first optical detection means 13.

The order in which the second optical detection means 14 and the third optical detection means 9 are arranged downstream of the chemical pickling means 3 is indifferent.

Preferably, rinsing means for rinsing the pickled strip are arranged between the chemical pickling means 3 and the second and/or third optical detection means 14, 9.

In all embodiments of the plant of the invention, there can be provided:

regeneration means 17 for regenerating an exhausted acid solution coming from the chemical pickling means 3 and obtaining a regenerated acid solution;

at least one pipe 18 to transport the exhausted acid solution from the chemical pickling means 3 to the regeneration means 17;

a first flow meter 4, preferably arranged along the pipe 18, for measuring the flow rate of said exhausted acid solution directed towards the regeneration means 17;

a first analyzer 6, preferably arranged along the pipe 18, for analyzing the concentration of acid and iron in the exhausted acid solution;

at least one pipe 19 to transport the regenerated acid solution from the regeneration means 17 to the chemical pickling means 3;

a second flow meter 5, preferably arranged along the pipe 19, for measuring the flow rate of the regenerated acid solution directed towards the chemical pickling means 3;

a second analyzer 7, preferably arranged along the pipe 19, for analyzing the concentration of acid and residual iron in the regenerated acid solution.

The regeneration means 17 comprise, for example, a chemical reactor in which iron in the form of an oxide is separated, by a pyrohydrolysis reaction, from the exhausted acid solution, which is then concentrated and returned for pickling. In the reactor, the exhausted acid solution (with high iron content) is heated in an oxidizing atmosphere which determines the vaporization of the solution, and while on the one hand the free acid is recovered, on the other hand, the iron is removed as an oxide.

This setup allows obtaining a mass balance of the chemical reaction required in order to completely remove the oxide layer, using the acid and iron concentration analyzers in the exhausted acid solution and the regenerated acid solution, which are continuously moved from and to the chemical pickling means 3, respectively. Indeed, these analyzers allow a further refinement of the pickling control as they allow calculating the amount of scale already removed by knowing, by means of well-known statistical models based on several treatments, the amount of initial oxide to be removed from the strip unwound from the coil.

Advantageously, a processing unit 10 is provided, configured to process the measurement data from at least the measurement means 11, possibly also from the measurement means 11', and the gaseous hydrogen detection means 12, and to adjust operating parameters of the chemical pickling means 3 accordingly.

Preferably, the processing unit 10 can also be configured to process strip cleaning level data from at least one of:

the first optical detection means 13, to possibly adjust the operating parameters of pickling of the last pickling tank;

and the second optical detection means 14 and/or the third detection means 9, to possibly further adjust the operating parameters of the chemical pickling means 3.

When the regeneration means 17 are provided, the processing unit 10 can also process data from the first flow meter 4, the first analyzer 6, the second flow meter 5, and the second analyzer 7, to adjust the operating parameters of the chemical pickling means 3 accordingly.

As for the metal strip cleaning method of the invention, which can be performed by the aforementioned plant, said method comprises the following steps:

a) unwinding at least one coil of rolled strip by means of the unwinding means 1;

b) measuring the thickness of the surface oxide layer of the rolled strip by means of the measuring means 11, 11';

c) pickling the rolled strip by means of the chemical pickling means 3.

In step b), the thickness of the oxide surface layer is measured, together with an analysis of the oxide composition, by means of at least one laser source associated with a respective optical fiber spectrometer, which defines a Laser-Induced Breakdown Spectroscopy (LIBS) system.

Advantageously, during step c), there is provided a detection of gaseous hydrogen in the fumes produced by the chemical pickling means 3 by means of said gaseous hydrogen detection means 12, preferably in the fumes produced by the last pickling tank 15, i.e., the one distal from the unwinding means 1.

The combined processing of the data coming from the measurement means 11 and the gaseous hydrogen detection means 12 and the consequent adjustment of operating parameters of the chemical pickling means 3, by means of the processing unit 10, surprisingly allows optimizing the pickling process.

Figure 2:
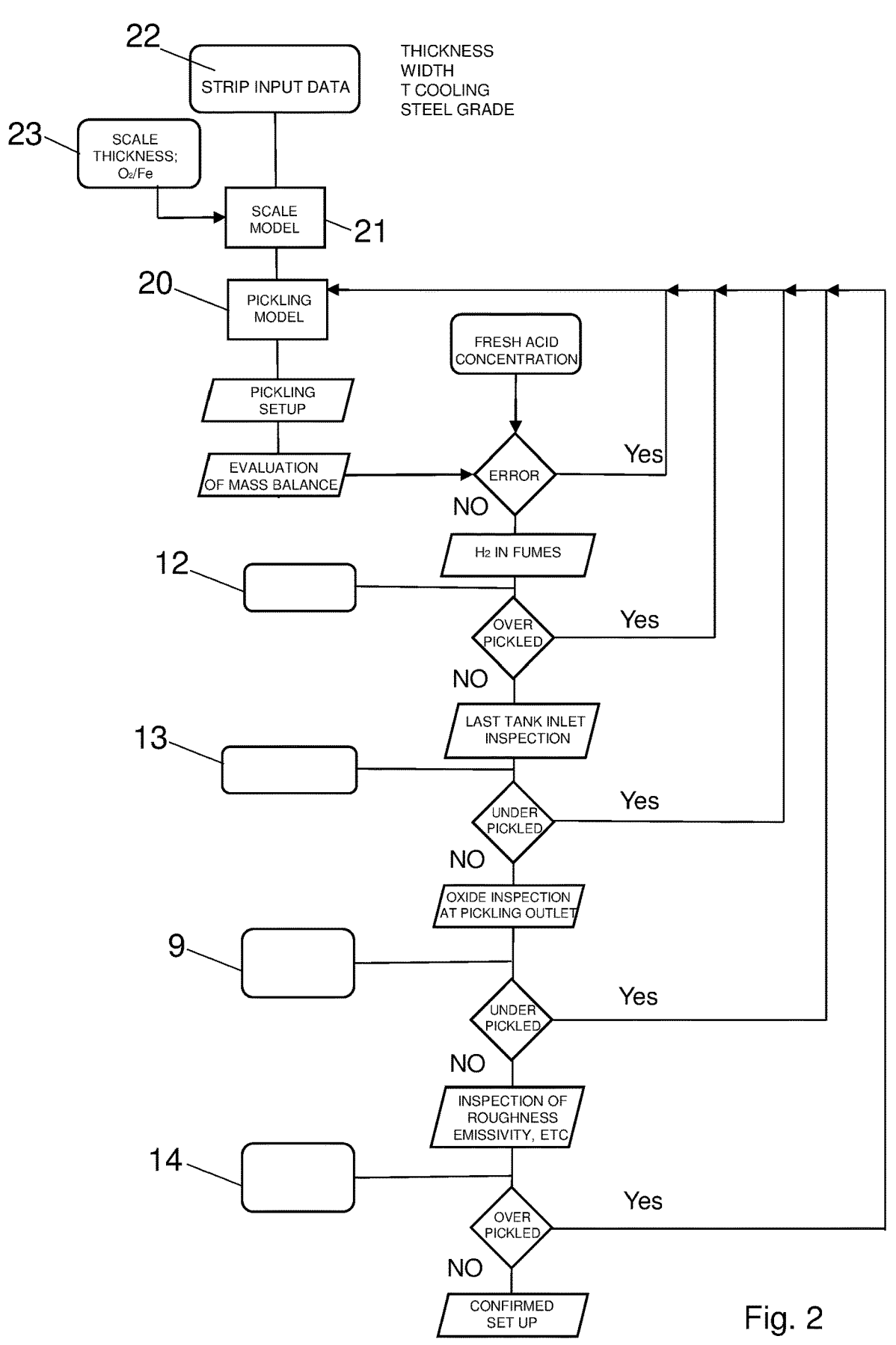
FIG. 2 shows a flowchart relating to an exemplary cleaning method according to the invention.

FIG. 2 shows an example of a flowchart of part of a cleaning method according to the invention.

Advantageously, the processing unit 10 uses a software, preferably installed in said processing unit 10, which includes a pickling adjustment model, or more simply pickling model, 20 configured to adjust one or more of the following pickling parameters, such as:

process speed, i.e., the strip feeding speed at which the strip travels through the pickling tanks;

concentrations of acid, e.g., hydrochloric acid, in the acid solution of the pickling tanks;

temperature of the acid solution in the pickling tanks;

turbulence level of the acid solution.

The pickling model 20 then generates a process setup and applies this latter to the strip which is entering the pickling tanks.

The pickling model 20 interacts with an oxide layer simulation model 21, or more simply oxide layer model or scale model 21, preferably included in said processing unit 10.

The oxide layer simulation model 21 produces simulation data of the oxide surface layer along the strip, in particular along the entire extension of the strip.

The pickling adjustment model 20 adjusts pickling parameters comprising the strip feeding speed in the chemical pickling means 3 and/or the turbulence level of the acid solution present in said chemical pickling means 3, preferably said pickling parameters further comprising the acid concentration in the acid solution and/or the temperature of said acid solution.

The simulation data are sent to the pickling adjustment model 20.

In order to produce the simulation data, the oxide layer simulation model 21 acquires both first input data 22, relating to the strip as wound on the coil, and second input data 23 consisting of the data detected by the measuring means 11, 11' during plant operation.

The first input data 22 comprises at least strip thickness, strip width, metal grade, strip winding temperature; while the second input data 23 comprises oxide surface layer thickness and oxide composition and preferably also the concentration of the oxide constituent elements.

The simulation data of the oxide surface layer along the strip is obtained by comparing the first input data 22 and the second input data 23 with a database containing data relating to a set of strips of different thickness, width, metal material and wound at different winding temperatures.

More in detail, the scale model 21 acquires first input data 22, such as the initial data of the strip as wound on the coil, which comprise strip thickness;

strip width;

steel grade;

strip winding temperature;

possible production data.

The scale model 21 also acquires, during the operation of the plant of the invention, the second input data 23 consisting of the data detected by the measuring means 11, 11', namely the thickness of the oxide surface layer, the oxide composition and the concentration of the oxide constituent elements, and in particular the presence of oxygen.

Using both the first input data 22 and the second input data 23, the scale model 21. e.g., by means of a comparison with a database preferably containing archived oxide measurements relating to a set of strips of different thickness, width, material and wound at different winding temperatures, generates a simulation of the amount of oxide present throughout the extension of the strip.

Preferably, the oxide surface layer simulation data comprises at least one of the following data:

thickness in micrometers;

weight in grams/m$^2$ of oxide to be removed;

estimation of the average oxide composition;

pickling coefficient of the strip.

As known, a pickling coefficient is defined as a coefficient Kd, the value of which is less than or equal to 1 but greater than 0.5. This value is used as a multiplication coefficient to define the strip feeding speed or pickling speed. The maximum speed will occur for Kd=1. For strips with difficult pickling Kd=0.5.

This information is sent to the pickling model 20 for defining the pickling parameters, such as those listed above, preferably customized for the head, center and tail of the strip to be processed. The pickling model 20 then generates the process setup.

At least one control loop is provided to improve the control of the pickling process. For each control loop, one or more values provided by the pickling model 20 are compared with the respective value measured or analyzed by a corresponding instrumentation installed along the plant. If the difference between the measured value and the value provided by the pickling model 20 does not exceed a threshold value (Error: NO), the model estimate is considered suitable and no feedback is generated. Conversely, if the difference between the measured value and the value provided by the pickling model 20 exceeds the threshold value (Error: YES), feedback requiring the pickling model 20 to generate a value offset to improve the process control is generated.

In the flowchart in FIG. 2, which relates to an exemplary variant of the plant of the invention in which, in addition to the measurement means 11, there are provided the regeneration means 17 with associated first flow meter 4, first analyzer 6, second flow meter 5, and second analyzer 7, the gaseous hydrogen detection means 12, the first optical detection means 13, the second optical detection means 14, the third optical detection means 9, the following control loops are cascaded on top of each other:

a first control loop to possibly adjust the mass balance of the chemical pickling reaction, which uses the values of the exhausted acid solution flow rate, the acid and iron concentration in the exhausted acid solution, the regenerated acid solution flow rate, and the acid and residual iron concentration in the regenerated acid solution, detected by the first flow meter 4, the first analyzer 6, the second flow meter 5, and the second analyzer 7, respectively;

a second control loop to possibly reduce/eliminate an over-pickling, indicated by the presence of possible gaseous hydrogen in the fumes of at least the last pickling tank, said presence being detected by the gaseous hydrogen detection means 12;

a third control loop to possibly reduce/eliminate an under-pickling, indicated by the presence of residual oxide on the surface of the strip entering the last pickling tank, said presence being detected by the first optical detection means 13;

a fourth control loop to possibly reduce/eliminate an under-pickling, indicated by the presence of residual oxide on the surface of the strip at the exit of the last pickling tank, said presence being detected by the third optical detection means 9;

a fifth control loop to possibly reduce/eliminate an over pickling, using the values of surface roughness and/or reflectivity and/or gray level and/or emissivity of at least one surface of the strip, detected by the second optical detection means 14.

The aforesaid second control loop provides that, if the difference between the gaseous hydrogen value in the fumes, detected by the gaseous hydrogen detection means 12, and the gaseous hydrogen value in the fumes provided by the pickling adjustment model 20 exceeds a predetermined threshold value, a feedback is produced, which requires the pickling adjustment model 20 to adjust at least one pickling parameter so that said difference does not exceed said threshold value. The first, third, fourth and fifth control loops, individually or all together, may be optional.

The invention claimed is:

1. A cleaning plant for cleaning rolled metal strips provided with an oxide surface layer, the plant comprising:

unwinding means for unwinding at least one coil of rolled strip;

chemical pickling means for pickling said rolled strip;

measuring means for measuring a thickness of the oxide surface layer, arranged between said unwinding means and said chemical pickling means;

wherein said measuring means comprise at least one laser source cooperating with an optical fiber spectrometer, defining a Laser-Induced Breakdown Spectroscopy (LIBS) system also adapted to analyze an oxide composition;

wherein gaseous hydrogen detection means are provided to detect a presence of gaseous hydrogen in fumes produced by said chemical pickling means;

wherein a processing unit is provided, adapted to process data from at least said measuring means and said gaseous hydrogen detection means, and adapted to adjust operating parameters of said chemical pickling means accordingly;

wherein said processing unit comprises:

an oxide layer simulation model, configured to produce simulation data of the oxide surface layer along the strip, by acquiring both first input data, relating to the strip as wound on the coil, and second input data consisting of data detected by the measuring means during plant operation;

a pickling adjustment model, configured to adjust pickling parameters comprising the strip feeding speed in the chemical pickling means and/or the turbulence level of the acid solution present in said chemical pickling means, said pickling parameters further comprising the acid concentration in the acid solution and/or the temperature of said acid solution;

wherein the simulation data are sent to the pickling adjustment model; and wherein at least one control loop is provided, configured so that, if the difference between a gaseous hydrogen value in the fumes, detected by the gaseous hydrogen detection means, and a gaseous hydrogen value in the fumes provided by the pickling adjustment model exceeds a threshold value, a feedback is produced requiring the pickling adjustment model to adjust at least one pickling parameter so that said difference does not exceed said threshold value.

2. The cleaning plant according to claim 1, wherein said chemical pickling means comprises two or more chemical pickling tanks, and wherein said gaseous hydrogen detection means are positioned to detect the presence of gaseous hydrogen in the fumes produced by at least the last chemical pickling tank.

3. The cleaning plant according to claim 2, wherein first optical detection means are provided to detect any residual oxide on a surface of the strip, said first optical detection means being arranged at the inlet of said last chemical pickling tank.

4. The cleaning plant according to claim 3, wherein further optical detection means are provided to detect a level of cleanliness of the rolled strip, arranged downstream of said chemical pickling means.

5. The cleaning plant according to claim 4, wherein said further optical detection means comprise second optical detection means to detect surface roughness and/or reflectivity and/or gray level and/or emissivity of at least one surface of the rolled strip.

6. The cleaning plant according to claim 5, wherein said further optical detection means further comprise third optical detection means to detect any residual oxide on the surface of the rolled strip.

7. The cleaning plant according to claim 6, wherein said processing unit is also adapted to process data from said first optical detection means, said second optical detection means and said third optical detection means, and to adjust the operating parameters of said chemical pickling means accordingly.

8. The cleaning plant according to claim 7, wherein there are provided:

regeneration means for regenerating an exhausted acid solution from the chemical pickling means and obtaining a regenerated acid solution;

a first flow meter for measuring a flow rate of said exhausted acid solution directed towards the regeneration means;

a first analyzer for analyzing a concentration of acid and iron in said exhausted acid solution;

a second flow meter for measuring a flow rate of said regenerated acid solution directed towards the chemical pickling means;

a second analyzer for analyzing a concentration of acid and residual iron in said regenerated acid solution;

wherein said processing unit is also adapted to process data at least from said first flow meter, said first analyzer, said second flow meter and said second analyzer, and to adjust the operating parameters of said chemical pickling means accordingly.

9. The cleaning plant according to claim 3, wherein said processing unit is also adapted to process data from said first optical detection means, and to adjust the operating parameters of said chemical pickling means accordingly.

10. The cleaning plant according to claim 9, wherein there are provided:

regeneration means for regenerating an exhausted acid solution from the chemical pickling means and obtaining a regenerated acid solution;

a first flow meter for measuring a flow rate of said exhausted acid solution directed towards the regeneration means;

a first analyzer for analyzing a concentration of acid and iron in said exhausted acid solution;

a second flow meter for measuring a flow rate of said regenerated acid solution directed towards the chemical pickling means;

a second analyzer for analyzing a concentration of acid and residual iron in said regenerated acid solution;

wherein said processing unit is also adapted to process data at least from said first flow meter, said first analyzer, said second flow meter and said second analyzer, and to adjust the operating parameters of said chemical pickling means accordingly.

11. The cleaning plant according to claim 5, wherein said processing unit is also adapted to process data from said first optical detection means and said second optical detection means, and to adjust the operating parameters of said chemical pickling means accordingly.

12. The cleaning plant according to claim 11, wherein there are provided:

regeneration means for regenerating an exhausted acid solution from the chemical pickling means and obtaining a regenerated acid solution;

a first flow meter for measuring a flow rate of said exhausted acid solution directed towards the regeneration means;

a first analyzer for analyzing a concentration of acid and iron in said exhausted acid solution;

a second flow meter for measuring a flow rate of said regenerated acid solution directed towards the chemical pickling means;

a second analyzer for analyzing a concentration of acid and residual iron in said regenerated acid solution;

wherein said processing unit is also adapted to process data at least from said first flow meter, said first analyzer, said second flow meter and said second analyzer, and to adjust the operating parameters of said chemical pickling means accordingly.

13. The cleaning plant according to claim 1, wherein said gaseous hydrogen detection means either comprise or consist of detection instruments adapted to perform thermal conductivity measurements.

14. The cleaning plant according to claim 1, wherein there are provided:

regeneration means for regenerating an exhausted acid solution coming from the chemical pickling means and obtaining a regenerated acid solution;

a first flow meter for measuring a flow rate of said exhausted acid solution directed towards the regeneration means;

a first analyzer for analyzing a concentration of acid and iron in said exhausted acid solution;

a second flow meter for measuring a flow rate of said regenerated acid solution directed towards the chemical pickling means;

a second analyzer for analyzing a concentration of acid and residual iron in said regenerated acid solution;

wherein said processing unit is also adapted to process data at least from said first flow meter, said first analyzer, said second flow meter, and said second analyzer, and to adjust the operating parameters of said chemical pickling means accordingly.

15. A method of cleaning metal strips, to be performed by a plant according to claim 1, comprising the following steps:

a) unwinding at least one coil of rolled strip by means of the unwinding means;

b) measuring the thickness of an oxide surface layer of the rolled strip by means of the measuring means;

c) pickling said rolled strip by means of the chemical pickling means;

wherein, in step b), a measurement of the thickness of the surface oxide layer is carried out, together with an analysis of the oxide composition, by means of at least one laser source associated with an optical fiber spectrometer, defining a Laser-Induced Breakdown Spectroscopy (LIBS) system; wherein said optical fiber spectrometer measures a presence of oxygen while a laser of said at least one laser source penetrates the surface oxide layer present on the rolled strip towards a non-oxidized base material, and the thickness of the surface oxide layer is equal to a depth excavated in the rolled strip, by the at least one laser source, when said optical fiber spectrometer detects an absence of oxygen;

wherein, in step c), there is provided a detection of gaseous hydrogen in the fumes produced by said chemical pickling means by means of the gaseous hydrogen detection means;

wherein there are provided the steps of processing data from both said measuring means and said gaseous hydrogen detection means and adjusting the operating parameters of said chemical pickling means accordingly, by means of the processing unit;

wherein said processing unit comprises:

an oxide layer simulation model, which produces simulation data of the oxide surface layer along the strip, by acquiring both first input data, relating to the strip as wound on the coil, and second input data consisting of data detected by the measuring means during plant operation;

and a pickling adjustment model, which adjusts pickling parameters comprising the strip feeding speed in the chemical pickling means and/or the turbulence level of the acid solution present in said chemical pickling means, said pickling parameters further comprising the acid concentration in the acid solution and/or the temperature of said acid solution;

wherein the simulation data are sent to the pickling adjustment model (20); and wherein at least one control loop is provided, according to which if the difference between a gaseous hydrogen value in the fumes, detected by the gaseous hydrogen detection means, and a gaseous hydrogen value in the fumes provided by the pickling adjustment model exceeds a threshold value, a feedback is produced requiring the pickling adjustment model to adjust at least one pickling parameter so that said difference does not exceed said threshold value.

16. The cleaning method according to claim 15, wherein the first input data comprises at least strip thickness, strip width, metal material grade, strip winding temperature; and wherein the second input data comprises surface oxide layer thickness and oxide composition.

17. The cleaning method according to claim 16, wherein the simulation data of the surface oxide layer along the strip is obtained by comparing said first input data and said second input data with a database containing data relating to a set of strips of different thickness, width, metal material and wound at different winding temperatures; wherein said simulation data comprises at least one of the following data:

thickness in micrometers;

weight in grams/$m^2$ of oxide to be removed;

estimation of an average oxide composition;

pickling coefficient of the rolled strip.

* * * * *